United States Patent [19]

Hallnemo et al.

[11] Patent Number: 4,990,534
[45] Date of Patent: Feb. 5, 1991

[54] ARALKYL ESTERS AND PROCESSES FOR THEIR PREPARATION

[75] Inventors: Gerd M. Hallnemo; Thomas Högberg; Ulf H. Lindberg; Bengt C. J. Ulff, all of Södertälje; Sven Ove Ögren, Nykvarn, all of Sweden

[73] Assignee: Aktiebolaget Astra, Sodertalje, Sweden

[21] Appl. No.: 305,728
[22] PCT Filed: May 24, 1988
[86] PCT No.: PCT/SE88/00271
  § 371 Date: Jan. 24, 1989
  § 102(e) Date: Jan. 24, 1989
[87] PCT Pub. No.: WO88/09327

PCT Pub. Date: Dec. 1, 1988

[30] Foreign Application Priority Data

May 27, 1987 [SE] Sweden .................. 8702228
Nov. 9, 1987 [SE] Sweden .................. 8704372

[51] Int. Cl.$^5$ ............................ A61U 31/24
[52] U.S. Cl. .................................... 514/534
[58] Field of Search ......................... 514/534

*Primary Examiner*—Stanley Friedman
*Attorney, Agent, or Firm*—White & Case

[57] ABSTRACT

Aralkyl esters are used to provide a potentiating effect on cholinergic responses.

1 Claim, No Drawings

ARALKYL ESTERS AND PROCESSES FOR THEIR PREPARATION

FIELD OF THE INVENTION

The object of the present invention is to provide novel compounds and therapeutically acceptable salts thereof with a selectively potentiating effect on cholinergic responses.

This invention also relates to processes for the preparation of the new compounds as well as to the pharmacological use of the new compounds and to pharmaceutical preparations containing such compounds.

PRIOR ART

U.S. Pat. No. 4 237 311 describes some aralkyl esters of amino acids e.g. alaproclate, which have effect on the central nervous system in man, especially an antidepressive activity combined with a reduced frequency of side effects. These compounds exert their effect by blocking the neuronal 5-hydroxytryptamine (5-HT) uptake. Furthermore it is known from U.S. Pat. No. 4 469 707 that some of the compounds, including alaproclate, described in U.S. Pat. No. 4 237 311 apart from being inhibitors of 5-hydroxytryptamine uptake also have a potentiating effect on cholinergic responses. Thus they are not selective for cholinergic potentiation. Further aralkyl esters of amino acids are described by Lindberg U. H. et al in the Journal of Medicinal Chemistry 21, p. 448–456 (1978).

OUTLINE OF THE INVENTION

According to the present invention it has been found that compounds of the general formula I

[Structure I: X,Y-phenyl-CH2-C(CH3)2-O-C(=O)-CH(R)-NH2]

in racemic or preferably in optically active form or a pharmaceutically acceptable salt thereof, wherein X and Y represent halogen, $CF_3$ or hydrogen provided that not both X and Y are hydrogen;

R represents a straight or branched saturated or unsaturated alkyl group having 2–5 carbon atoms, with the proviso that the racemate of the compound wherein X is 4-Cl, Y is H and R is —CH(CH3)2 is excluded, exhibit a selectively potentiating effect on central cholinergic responses. This potentiation is probably mediated by effects on ion-channels, most likely of potassium type. The influence on ion-channels coupled to various receptors makes it possible to use the compounds defined above in the treatment of mental disturbances e.g. psychosis, schizophrenia, schizoaffective conditions, anxiety, unipolar and bipolar depression as well as in the treatment of minimal memory impairment (MMI) and of senile dementia of the Alzheimer type (SDAT). The latter two MMI and SDAT are regarded as associated with a cholinergic dysfunction.

Halogen is preferably chloro, bromo or fluoro, in the para and meta positions and in particular the para position when monosubstituted, that is when one of X and Y is hydrogen.

Especially preferred are compounds wherein X is para-substituted fluoro or chloro or X and Y are both chloro, Y is H and R is a branched alkyl group or ethyl and propyl when not branched.

Most preferred are the following compounds

[Structure: X-phenyl-CH2-C(CH3)2-O-C(=O)-CH(NH2)-CH2-CH(CH3)2, wherein X is Cl or F]

[Structure: F-phenyl-CH2-C(CH3)2-O-C(=O)-CH(NH2)-CH2-CH(CH3)2 (S)-form]

[Structure: Cl-phenyl-CH2-C(CH3)2-O-C(=O)-CH(NH2)-CH(CH3)2 (S)-form]

[Structure: 3,5-diCl-phenyl-CH2-C(CH3)2-O-C(=O)-CH(NH2)-CH(CH3)2]

[Structure: Cl-phenyl-CH2-C(CH3)2-O-C(=O)-CH(NH2)-C2H5]

[Structure: Cl-phenyl-CH2-C(CH3)2-O-C(=O)-CH(NH2)-CH2-CH=CH2]

and

[Structure: Cl-phenyl-CH2-C(CH3)2-O-C(=O)-CH(NH2)-C3H7 (R/S)- or (S)-form]

Illustrative examples of the substituents in the general formula I are given in the examples and in Table 1.

TABLE 1

[Structure header: X,Y-phenyl-CH2-C(CH3)2-O-C(=O)-CH(R)-NH2]

| Compound according to Example No | X | Y | R |
|---|---|---|---|
| 1,9 | 4-Cl | H | C2H5 |
| 2,23,24 | 4-F | H | C2H5 |
| 3 | 4-F | H | C3H7 |
| 4,8 | 4-Cl | H | C3H7 |
| 5 | 4-Cl | H | CH2—CH=CH2 |
| 6 | 4-Cl | H | (CH2)4CH3 |

TABLE 1-continued

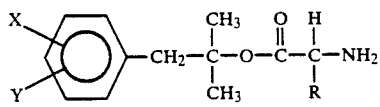

| Compound according to Example No | X | Y | R |
|---|---|---|---|
| 7 | 4-Cl | H | CH$_2$C≡CH |
| 11 | 4-Cl | H | CH$_2$CH(CH$_3$)$_2$ |
| 12 | 4-Cl | H | CH(CH$_3$)(C$_2$H$_5$) |
| 13 | 4-F | H | CH(CH$_3$)$_2$ |
| 14,25 | 3-Cl | 5-Cl | CH(CH$_3$)$_2$ |
| 15 | 4-F | H | CH(CH$_3$)(C$_2$H$_5$) (SS/RS) |
| 16,22 | 3-Cl | 4-Cl | C$_2$H$_5$ |
| 17 | 4-F | H | CH$_2$CH(CH$_3$)$_2$ |
| 18 | 3-CF$_3$ | H | C$_2$H$_5$ |
| 19 | 3-CF$_3$ | H | C$_3$H$_7$ |
| 20 | 4-F | H | CH$_2$CH(CH$_3$)$_2$ (S) |
| 26,28 | (+)4-Cl | H | CH(CH$_3$)$_2$ |
| 27 | (−)4-Cl | H | CH(CH$_3$)$_2$ |
| 10 | 4-Cl | H | C$_3$H$_7$ (R) |
| 21 | 4-Cl | H | C$_3$H$_7$ (S) |

PREPARATION

The compounds with the general formula I in optically active form or in racemic form

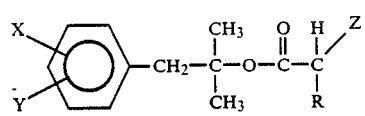 I wherein X, Y and R are as defined above are prepared (A) by converting the corresponding derivatives II having the identical R group,

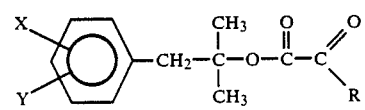 II wherein X, Y and R are as defined above and Z represents a group which can be transformed to an NH$_2$-group, by a suitable hydrolytic, reductive, electrochemical or other known process (B) by reacting an -ketoester of the formula III

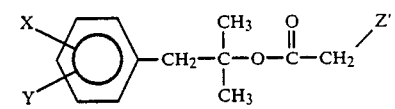 III wherein X, Y and R are as defined above with ammonia, an ammonium salt or a suitable amine derivative in the presence of a suitable reducing agent in a stepwise or direct manner, whereby I is obtained, (C) by rearrangement in an aqueous medium of a compound of the formula IV

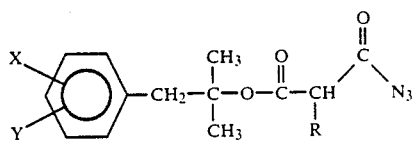 IV wherein X, Y and R are as defined above, with or without the presence of a catalyst (D) by reduction of a compound of the general formula I

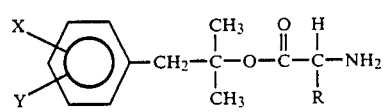 I wherein X and Y are as defined above and R is an unsaturated alkyl, straight or branched containing 2-5 carbon atoms to the corresponding compounds wherein R is a saturated alkyl group, or (E) by resolution of the racemate.

According to process A the group Z in compound II is especially easily cleavable chiral or non-chiral amides, imides, carbamates, isocyanate, silyl derivatives, imines, enamines, allylic or benzylic amines or other known amine protecting groups. Such groups can be trifluoroacetamide, formamide, o-nitrophenylacetamide, 3-(o-nitrophenyl)propanamide, o-nitrobenzamide, phtalimide, p-methoxybenzyl, benzyl, t-butyl and 1,1-dimethyl-2-chloroethylcarbamates, 2,2,5,5-tetramethyl-1-aza-2,5-disilolidine (stabase adduct), N-benzylideneamine, N-(diphenylmethylene)amine, chiral Schiff bases, such as (1S,2S,5S)- or (1R,2R,5R)-2-hydroxy-pinanyl-3-ideneamines, N-(acylvinyl)amine, N-benzylamine, N-di(p-methoxyphenyl)methylamine. Furthermore Z can be groups such as nitro, azido, oxime, hydrazine or imine, which can be transformed to NH$_2$ by known reductive processes.

The starting compounds II are prepared by one of the following methods:

(i) α-Alkylation of a protected glycine ester of the formula V $$\text{[structure V]}$$ V wherein X, Y are as defined above and Z' is a suitable group chosen from Z as defined above, preferably silyl derivatives (e.g. 2,2,5,5-tetramethyl-1-aza-2,5-disilolidine), imines (e.g. N-(diphenyl)methyleneamine) or chiral imines (e.g. (1S,2S,5S)- or (1R,2R,5R)-2-hydroxypinanyl-3-ideneamine. The latter chiral imines are used for the synthesis of enantiomerically enriched material. The alkylation can preferably be made in two ways namely:

(a) A protected glycine enolate can be produced by reaction of the compound of the formula V with a hindered base, such as lithium diisopropylamide at low temperature (e.g. −78° C.) in an inert solvent such as tetrahydrofuran with or without a complexing agent, e.g. tetramethylethylenediamine (TMEDA) followed by the addition of a compound of the formula VI

R—X' VI wherein X' is a suitable leaving group, such as I, Br, Cl or p-toluenesulfonyl and R is as defined above; or (b) The glycine enolate is trapped with e.g. (CH₃)₃SiCl to give a silyl ketene acetal, which after transfer to a solvent such as CH₂Cl₂ is reacted with a compound of the formula VI in the presence of a Lewis acid, such as TiCl₄ or ZnBr₂;

(ii) Condensation of an alcohol of the formula VII

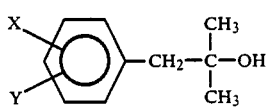

wherein X and Y are as defined above with a suitably protected amino acid or derivative thereof of the formula VIII

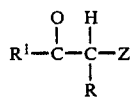

wherein Z is as defined above and R¹ is a halogen such as Cl or Br, a mixed anhydride with inorganic acids or their esters or an organic acid or a hydroxy group in combination with a coupling agent, such as dicyclohexylcarbodiimide combined with (dimethylamino)pyridine, or triphenyl phosphine dibromide. The latter procedure with R¹=OH is preferred in the synthesis of enantiomerically enriched material;

(iii) Reaction of a compound of the formula IX

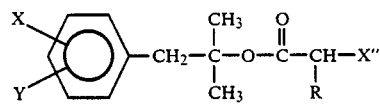

wherein X and Y are as defined above and X" is a suitable leaving group, such as I, Br, Cl or p-toluenesulfonyl, with a nitrogen nucleophile, which preferably is N₃—, NO₂—, phtalimide⁻, hexamethylenetetramine, NH₃, isocyanate or dibenzylamine;

(iv) Reaction of the keto ester with the formula III above with hydroxylamine or an amine derivative according to a process known in the art to give the oxime or the corresponding imine derivative;

(v) Reaction of the ester enolate or the silyl enol ether of the ester of the formula X

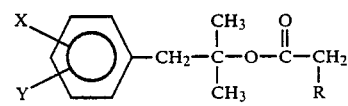

wherein X, Y and R are as defined above, with a suitable masked nitrogen electrophile, such as a dialkylazadicarboxylate; or (vi) Conversion of an acid of the formula XI

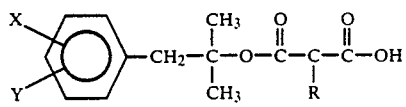

or a derivative thereof to a cleavable carbamate via rearrangement of the corresponding acyl azide. The acid can for example be reacted with a reagent such as diphenylphoshorylazide in the presence of a tertiary amine in t-butanol to produce the Boc-protected amine. (Boc=tertiary butoxycarbonyl).

The compounds of the formula II produced by one of the methods (i)-(vi) can be isolated as such and subsequently converted to a compound of the formula I or the compounds of the formula II can be generated in situ and converted to a compound of the formula I without isolation.

Depending upon the specific nature of R and Z and whether the compounds are enantiomerically enriched or not the above mentioned methods (i)-(vi) to produce a compound of the formula II have advantages and limitations, which are obvious to a person skilled in the art.

According to process B the reducing agent is preferably sodium cyanoborohydride, sodium borohydride or hydrogen in the presence of a catalyst e.g. Raney Nickel, Pd/C or Pt. It is especially preferred to perform the reaction with ammonium acetate in methanol with sodium cyanoborohydride as the reducing agent.

When the compounds of the formula I are enantiomerically enriched, this can be accomplished by a synthesis directly giving an optically active compound I or a suitable intermediate, or by resolution of racemic I or a suitable intermediate by known processes including chromatographic methods with or without derivatization or by fractional crystallization.

The resolvation of I can be accomplished by recrystallization of a diastereomeric salt such as L-(+) or D-(−)-tartrate.

PHARMACEUTICAL PREPARATIONS

According to the present invention the compounds of the formula I will normally be administered orally, rectally or by injection, in the form of pharmaceutical preparations comprising the active ingredient either as a free base or a pharmaceutically acceptable non-toxic, acid addition salt, e.g. the hydrochloride, hydrobromide, lactate, acetate, phosphate, sulphate, sulphamate, citrate, tartrate, oxalate and the like in a pharmaceutically acceptable dosage form. The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical preparations containing a compound of the formula I in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain, e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substance or different amounts of the active compounds.

For the preparation of soft gelatine capsules, the active substance may be admixed with e.g. a vegetable oil or polyethylene glycol. Hard gelatine capsules may contain granules of the active substance using either the above-mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example, solutions containing from about 0.2% to about 20% by weight of the active substance herein described, the balance being sugar and mixture of ethanol, water, glycerol, and propylene glycol. Optionally such liquid preparations may contain colouring agents, flavouring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules.

Suitable daily doses of the compounds of the invention in therapeutical treatment of humans are 100 to 500 mg at peroral administration and 20 to 100 mg at parenteral administration.

It is especially preferred to administer one of the enantiomers of the compound of the formula

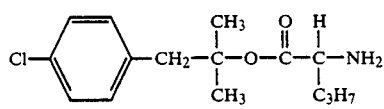

and especially the (S)-enantiomer.

EXAMPLES

Example 1 (Method A)

1-(4-Chlorophenyl)-2-methyl-2-propyl 2-aminobutanoate

To a solution of 3.6 g (0.015 mol) of 1-(4-chlorophenyl)-2-methyl-2-propyl glycinate and 8.5 ml triethylamine in 40 ml of dry $CH_2Cl_2$ under $N_2$ 4.0 g (0.018 mol) of di(chlorodimethylsilyl)ethane dissolved in 10 ml of dry $CH_2Cl_2$ was added dropwise with a syringe. After stirring for 1.5 h at room temperature 100 ml of hexane was added and the hydrochloride was filtered off. Evaporation of the solvent gave 5.23 g of a crude product (stabase adduct of the starting compound), $^1H$ NMR (60 MHz $CDCl_3$ crude product) δ ppm 7.3 (AA'BB', 4, $C_6H_4$), 3.5 (s, 2, $COCH_2$), 3.1(s, 2, benzylic), 3.2(s, 6, $C(CH_3)_2$), 0.8 (s, 4, $CH_2CH_2$), 0.03(s, 12, $Si(CH_3)_2$), which was used immediately in the next step.

To a solution of lithium diisopropylamide prepared from diisopropyl amine (1.1 ml, 7.8 mmol) and butyl lithium (7.8 mmol in hexane) in 20 ml dry THF, and $N,N,N^1,N^1$-tetramethylethylenediamine (1.16 ml, 7.8 mmol) a solution of the stabase adduct (2.38 g, 6.2 mmol) in 15 ml dry THF was added with a syringe at $-20°$ C. under $N_2$ during 0.5 h. The mixture was stirred for 1.5 h and $^1H$ NMR examination of a sample quenched with $D_2O$ showed complete litniation. Iodoethane (2.6 ml, 31.2 mmol) was added at $-10°$ C. and the mixture was stirred for 2.5 h at $-10°$ C. Concentrated ammonia (5 ml) and $H_2O$ (100 ml) were added to quench the excess iodo ethane. The mixture was extracted twice with hexane or diethyl ether, the organic phase was dried and the solvent evaporated to give 2.26 g crude product containing 83% of the ethylated stabase adduct. $^1H$ NMR (60 MHz, $CDCl_3$) δ ppm 7.3(m, 4, $C_6H_4$), 3.3(t, 1, COCH, J=7Hz), 3.0(s, 2, benzylic), 0.8(t, 3, $CH_2CH_3$), 0.8(s, 4, $CH_2CH_2$), 0.1(s, 12, $Si(CH_3)_2$).

The crude stabase adduct of the title compound was dissolved in ether and hydrolyzed by extraction with 1M HCl. The aqueous phase was made alkaline and extracted twice with diethyl ether. Drying and evaporation gave 1.15 g of the crude amine, which was purified by flash chromatography with hexane: ethyl acetate 1:1 and 5% trietylamine as eluent to give 0.8 g of 1-(4-chlorophenyl)-2-methyl-2-propyl 2-aminobutanoate $^1H$ NMR (200 MHz $CDCl_3$) δppm 7.26 and 7.12 (AA'BB', 4, $C_6H_4$ J=8.3 Hz), 3.04(dd, 1, CH, J=5.6, 6.8 Hz), 3.07, 2.98(AB, 2, benzylic J=13.9 Hz) 1.59(m, 2, $CH_2$), 1.48(s, 3, $CCH_3$), 1.44(s, 3, $CCH_3$), 0.91(t, 3, $CH_3$ J=7.33 Hz).

The hydrochloride salt was precipitated from diethyl ether and recrystallized from $CH_3CN$. Yield 0.8 g, m.p. 125°–126.5° C.

In an analogous way the following compounds were prepared;

Example 2

1-(4-fluorophenyl)-2-methyl-2-propyl 2-aminobutanoate $^1H$ NMR (200 MHz, $CDCl_3$)δppm 7.15, 6.97(m, 4, $C_6H_4$, J=5.4, 8.6 Hz), 3.26(dd, 1, CH, J=5.6, 6.8 Hz), 3.06, 2.97(AB, 2, benzylic J=13.7 Hz), 1.92(s, 2, $NH_2$), 2.65(m, 2, $CHCH_2$), 1.48 (s, 3, $CCH_3$), 1.44(s, 3, $CCH_3$), 0.90 (t, 3, $CH_2CH_3$ J=7.6 Hz).

M.p. HCl salt. 141°–142° C.

Example 3

1-(4-fluoropnenyl)-2-methyl-2-propyl 2-aminopentanoate $^1H$ NMR (200 MHz, $CDCl_3$)δ ppm 7.13, 6.97 (m, 4, $C_6H_4$, J=5.5, 8.7 Hz), 3.3(dd, 1, CH, J=5.4, 7.1 Hz), 2.99, 2.97 (AB, 2, benzylic, J=13 Hz), 1.48, (s, 3, $CCH_3$), 1.44(s, 3, $CCH_3$), 1.4(m(hidden), 4, $CH_2CH_2$), 1.4(hidden, 2, $NH_2$), 0.90(t, 3, $CH_2CH_3$, J=6.8 Hz).

M.p. HCl salt 118.0°–119.5° C.

Example 4

1-(4-Chlorophenyl)-2-methyl-2-propyl 2-aminopentanoate $^1$H NMR (200 MHz, CD$_3$OD) HCl salt δppm 7.41 and 7.32(AA'BB', 4, C$_6$H$_4$ J=8.8 Hz), 3.99(t, 1, CH, J=6.4 Hz), 3.23, 3.15(AB, 2, benzylic, J=14.1 Hz), 1.82, 1.42(m, 4, CH$_2$CH$_2$), 1.46(s, 3, CCH$_3$), 1.42(s, 3, CCH$_3$), 1.00(t, 3, CH$_2$CH$_3$, J=7.3 Hz)

M.p. HCl salt 113.5°–116.0° C.

Example 5

1-(4-Chlorophenyl)-2-methyl-2-propyl 2-amino-4-pentenoate

M.p. (HCl salt) 132.5°–133.5° C.

$^1$H NMR (200 MHz, CD$_3$OD) HCl salt δppm 7.31, 7.22(AA'BB', 4, C$_6$H$_4$ J=8,8 Hz), 5.67(m, 1, allylic CH=CH$_2$), 5.15(m, 2, allylic CH=CH$_2$), 3.97(t, 1, CH, J=6.35 Hz), 3.15, 3.03(AB, 2, benzylic, J=14 Hz), 2.58(m, 2, CH$_2$), 1.56 (s, 3, CCH$_3$), 1.49(s, 3, CCH$_3$).

Example 6

1-(4-Chlorophenyl)-2-methyl-2-propyl 2-aminoheptanoate

M.p. (HCl salt) 122°–126° C.

$^1$H NMR (200 MHz, CDCl$_3$) δppm 7.25, 7.12(AA'BB', 4, C$_6$H$_4$, J=8.3 Hz), 3.29(dd, 1, CH, J=6.3 Hz), 3.06, 2.96(AB, 2, benzylic, J=14 Hz), 1.54(s, 2, NH$_2$), 1.48(s, 3, CCH$_3$), 1.44(s, 3, CCH$_3$), 1.5, 1.26(m, 8(CH$_2$)$_4$), 0.88(t, 3, CH$_2$CH$_3$ J=6.35 Hz).

Example 7

1-(4-Chlorophenyl)-2-methyl-2-propyl 2-amino-4-pentynoate

M.p. (HCl salt) 162.0°–163.5° C.

$^1$H NMR (200 MHz, CDCl$_3$) δppm 7.26, 7.13(AA'BB', 4, C$_6$H$_4$, J=8.6 Hz) 3.49(dd, 1, CH, J=5.3, 6.1 Hz), 3.05(s, 2, benzylic), 2.55(dd, 1, HCH, J=5,2, 2,7 Hz), 2.30(dd, 1, HCH, J=6.1, 2.7 Hz), 2.05(t, 1, =CH, J=2.7 Hz), 1.71(s, 2, NH$_2$), 1.48(s, 3, CCH$_3$), 1.46(s, 3, CCH$_3$).

Example 8 (Method A)

1-(4-Chlorophenyl)-2-methyl-2-propyl 2-aminopentanoate

Benzophenone imine (0.8 g, 2.9 mmol) and finely ground 1-(4-chlorophenyl)-2-methyl-2-propyl glycinate hydrochloride and 10 ml of CH$_2$Cl$_2$ were stirred at room temperature over night with the exclusion of moisture (CaCl$_2$ tube). The reaction mixture was filtered to remove NH$_4$Cl, and evaporated to dryness. The residue was taken up in 10 ml of ether, washed with water and dried. Filtration and removal of the solvent were followed by flash chromatography on SiO$_2$ saturated with NH$_3$ (methanol/NH$_3$) with hexane: ethyl acetate 97:3 as eluent to yield 0.8 g (63%) of 1-(4-chlorophenyl)-2-methyl-2-propyl N-(diphenylmethylene)glycinate. $^1$H NMR (CDCl$_3$, 60 MHz) δppm 7.5(m, 10, arom), 4.2(s, 2, N-CH$_2$), 3.1(s, 2, benzylic), 1.5(s, 6, C(CH$_3$)$_2$).

To a solution of lithiumdiisopropylamide prepared from diisopropylamine (0.35 ml, 2.45 mmol) and butyl lithium (2.45 mmol in hexane) in 30 ml dry THF and DMEU (1,3-dimethyl-2-imidazolidinone) (3 ml) a solution of 1-(4-chlorophenyl)-2-methyl-2-propyl N-(diphenylmethylene)glycinate (0.8 g, 1.97 mmol) in 10 ml dry THF was added dropwise at −78° C. under N$_2$. After 1 h iodopropane (0.6 ml, 6 mmol) was added. After 4 h at room temperature the reaction mixture was partitioned between ether and ice cold diluted Na$_2$CO$_3$ solution. The ether was dried and evaporated to give 0.9 g of 1-(4-chlorophenyl)-2-methyl-2-propyl 2-[(diphenylmethylene) amino] pentanoate as an oil. $^1$H NMR (200 MHZ, CDCl$_3$) δppm 7.8, 7.4, 7.1(m, 14, arom), 3.93(t, 1, CH, J=6.3 Hz), 0.82(t, 3, CH$_2$CH$_3$ J=7.4 Hz).

The crude oil (0.9 g) from the preceding step was dissolved in 10 ml of diethyl ether and 10 ml of 1M HCl was added. The two-phase mixture was stirred for two hours at room temperature. The aqueous phase was made alkaline and extracted twice with diethyl ether. Drying and evaporation gave the crude amine, which was purified with flash chromatography using hexane: ethyl acetate in proportions 4:6 with 5% TEA as eluent to give 0.36 g (63%) of the title product. The hydrochloride salt was precipitated and recrystallized from CH$_3$CN. Yield 0.3 g. mp. 113.5°–116.0° C. $^1$H NMR was the same as according to Example 4.

Example 9 (Method A)

1-(4-Chlorophenyl)-2-methyl-2-propyl 2-aminobutanoate

A mixture of 1-(4-chlorophenyl)-2-methyl-2-propyl glycinate (0.73 g, 3 mmol) and (1S, 2S, 5S)-(-(-2-hydroxypinan-3-one (0.50 g, 2.95 mmol) in benzene (15 ml) containing boron trifluoride (2 drops) and crushed, activated molecular sieves was refluxed for 4 h under nitrogen. Filtration followed by evaporation gave 1.1 g of the Schiff base as an oil, which was used directly in the next step. $^1$H NMR (200 MHz, CDCl$_3$) δppm 7.25, 7.14 (AA'BB', 4, C$_6$H$_4$), 4.05(s, 2,

3.10 (s, 2, benzylic) To lithiumdiisopropylamide (4 mmol) in THF (3 ml) the above isolated Schiff base (0.78 g, 2 mmol) was added in THF at −78° C. under nitrogen and the mixture was stirred for 2 hr to form the dianion. After the addition of iodoethane (0.4 ml. 5 mmol) the mixture was stirred over night and allowed to reach room temperature.

Benzene (30 ml) and 15% aqueous citric acid (3.2 ml) were added and the benzene layer was washed with saturated aqueous sodium chloride. Drying and evaporation gave 0.9 g of the alkylated Schiff base as an oil.

$^1$H NMR (200 MHz, CDCl$_3$) δppm 7.25, 7.11(AA'BB', 4, C$_6$H$_4$), 3.97(dd, 1,

J=5.8, 7.0 Hz), 3.05(s, 2, benzylic), 0.87(t, 3, CH$_2$CH$_3$).

The crude product (0.2 g) from the preceding step was dissolved in THF(14 ml). After the addition of 15% aqueous citric acid (10 ml) the mixture was stirred at room temperature for 72 h. The THF was evaporated and the aqueous layer was extracted with benzene. The benzene layer was extracted with 0.5M HCl. The combined aqueous layers were made alkaline with potassium carbonate and extracted with diethyl ether. The ether phase was dried and the diethyl ether was evaporated to give 0.05 g of the title compound. The enantiomeric excess (abbreviated e.e.) was determined by capillary GC after coupling with Moshers acid to 80% e.e. of the (R)-isomer. The product obtained was precipitated as a HCl salt. M.p. 125°-127° C. $^1$H NMR was the same as according to Example 1.

Example 10

1-(4-Chlorophenyl)-2-methyl-2-propyl (R)-2-aminopentanoate.

[2-Hydroxypinanyl-3-indene]-2-aminopentanoic acid 1-(4-chlorophenyl)-2-methyl-2-propylester (8,17 g) prepared analogous to steps 1 and 2 in example 9 was dissolved in pyridine (50 ml) and hydroxylammoniumsulfate (15.4 g) and water (5 ml) were added. The mixture was stirred at room temperature for 18 h. After addition of water (40 ml) and extraction with diethyl ether the organic phase was dried and evaporated. The crude product was chromatographed using etyl acetate: hexane and 5% of triethylamine as eluent to yield 1.85 g (35%) of the product as an oil. E.e. 86% of (R)-isomer. Precipitation with D-(−)-tartaric acid and recrystallization from ethanol: water 2:1 gave 1.05 g of the tartrate. E.e. >97%. Mp 122°-125° C.

$^1$H NMR (200 MHz, CDCl$_3$) δppm 7.26, 7.12(AA'BB', 4, C$_6$H$_4$), 3.30(dd, 1, CH, J=5.1 Hz), 3.02(AB, 2, benzylic, J=13.4 Hz) 1.48(s, 5, CCH$_3$+NH$_2$), 1.44(s, 3, CCH$_3$) 1.6–1.3(m, 4, CH$_2$CH$_2$), 0.94(t, 3, CH$_3$, J=7.3 Hz)

Example 11 (Method A)

1-(4-Chlorophenyl)-2-methyl-2-propyl 2-amino-4-methylpentanoate.

Leucine (3 g, 0.023 mol) and phtalic anhydride (3.38 g, 0.023 mol) were mixed and heated in an oil bath, wherein the temperature was slowly rising to 160° C. After 4 h the oil bath was removed. The white solid was crystallized from hexane, to give 4.8 g (80%) N-phtaloyl leucine. $^1$H NMR(200 MHz, CDCl$_3$) δppm 7.85, 7.72(AA'BB', 4, C$_6$H$_4$), 5.0(dd, 1,

J=11.5, 4.4 Hz), 2.37(ddd, 1, H-CH, J=14.4, 11.5, 4.1 Hz), 1.95(ddd, 1, H-C-H, J=14.4, 10.0, 4.4 Hz), 1.48(m, 1, CH(CH$_3$)$_2$), 0.95(d, 3, CH$_3$, J=4.4 Hz), 0.92(d, 3, CH$_3$, J=4.4 Hz).

N-Phtaloyl leucine (3.7 g, 14.2 mmol) obtained above and thionyl chloride (16.4 ml, 56.8 mmol) were refluxed for 3 hours. The excess thionyl chloride was evaporated. 4×30 ml of CH$_2$Cl$_2$ was added and evaporated in order to remove all thionyl chloride from the N-phtaloyl leucine acid chloride. Yield: 4 g (78%) $^1$H NMR(200 MHz, CDCl$_3$) δppm 7.93, 7.81(AA'BB', 4, C$_6$H$_4$), 5.13(dd, 1,

J=4.4, 11.2 Hz), 2.38(ddd, 1, H-C-H, J=4.4, 11.2, 14.2 Hz), 2.05(ddd, 1, H-C-H, J=4.4, 10.3, 14.2 Hz), 1.53(m, 1, CH(CH$_3$)$_2$, 0.98(d, 3, CH$_3$, J=3.4 Hz), 0.94(d, 3, CH$_3$, J=3.4 Hz).

1-(4-chlorophenyl-2-methyl-2-propanol (2.62 g, 14.2 mmol) and DMAP (0.17 g, 1.42 mmol) were dissolved in 30 ml of THF and triethylamine (2 ml, 14.3 mmol) was added. The N-phtaloyl leucine acid chloride (4 g, 14.3 mmol) dissolved in 20 ml of THF was added dropwise during 3 h. After 16 h the reaction mixture was diluted with 100 ml 1M HCl and 100 ml CH$_2$Cl$_2$. The organic phase was washed with 100 ml 0.5M NaOH and 100 ml H$_2$O, whereafter it was dried and evaporated. The resulting dark oil was filtered through a silica plug using hexane: ethyl acetate 9:1 and 5% of triethylamine as eluant, to give 1-(4-chlorophenyl)-2-methyl-2-propyl 2-[(N-phtaloyl)amino]-4-methylpentanoat. 3.75 g (60%).

$^1$H NMR (200 MHz, CDCl$_3$) δppm 7.85, 7.76(AA'BB', 4, C$_6$H$_4$), 7.05, 6.95(AA'BB', 4, ClC$_6$H$_4$), 4.85(dd, 1,

J=4,4, 11.5 Hz) 3.01, 2.82(AB, 2, benzylic, J=13.9 Hz), 2.2(ddd, 1, H-C-H, J=4.2, 11.5, 14.0 Hz), 1.84(ddd, 1, H-C-H, J=4.4, 10.3, 14.0 Hz), 1.51(s, 3, CCH$_3$), 1.5(hidden, 1, CH(CH$_3$)$_2$), 1.42(s, 3, CCH$_3$), 0.94(d, 3, CH(CH$_3$), J=6.6 Hz), 0.91(d, 3, CH(CH$_3$), J=6.4 Hz).

The 1-(4-chlorophenyl)-2-methyl-2-propyl 2-[(N-phtaloyl)amino]-4-methylpentanoat (0.9 g, 2, 1 mmol) was dissolved in 15 ml of methanol. Hydrazine hydrate (0.5 ml) dissolved in 5 ml of methanol was added dropwise at 0° C. The reaction was followed by GC. After 4 h the methanol was evaporated and diethyl ether (2.5 ml) was added to the residue. After filtration the diethyl ether was evaporated and the residue was chromatographed using ethyl acetate: hexane 25:75 and 5% of triethylamine as eluent.

Yield: 0.45 g (75%).

The title product was precipitated as an oxalate from diethyl ether to give the title compound which was recrystallized from i-propanol. Yield: 0.42 g M.p. (oxalate) 142.0°-144.0° C.

$^1$H MNR (200 MHz, CD$_3$OD) oxalate δppm 7.39, 7.31(AA'BB', 4, C$_6$H$_4$), 3.89(t, 1,

J=7.3 Hz) 3.15(s, 2, benzylic), 1.7, 1.65(m, 3, CH$_2$CH), 1.63(s, 3, CCH$_3$), 1.60(s, 3, CCH$_3$), 1.0(d, 6, CH(CH$_3$)$_2$, J=6 Hz).

The compounds according to the following Examples 11-18 were prepared according to the methods described above:

Example 12

1-(4-Chlorophenyl)-2-methyl-2-propyl 2-amino-3-methylpentanoate

M.p. (oxalate) 124.0°-125.5° C. $^1$H NMR (200 MHz, CD$_3$OD) oxalate δppm 7.41, 7.37(AA'BB', 4, C$_6$H$_4$), 3.99(t, 1, COCH, J=4.4 Hz), 3.26, 3.09(AB, 2, benzylic J=13.7 Hz), 2.05(m, 1,

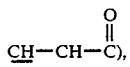

1.67(s, 3, CCH$_3$), 1.57(s, 3, CCH$_3$), 1.6, 1.45(m, 2, CH$_2$CH$_3$), 1.07(d+t, 5, CH$_3$CH$_2$+CH$_3$CH).

Example 13

1-(4-Fluorophenyl)-2-methyl-2-propyl 2-amino-3-methylbutanoate

M.p. oxalate 137.0°–139.5° C. ¹H NMR (200 MHz, CD₃OD) oxalate δppm 7.34, 7.11(m, 4, C₆H₄), 3.90(d, 1, COCH, J=4.4 Hz), 3.26, 3.09 (AB, 2, benzylic, J=13.6 Hz), 2.37 (m, 1, CH), 1.65(s, 3, CCH₃), 1.56(s, 3, CCH₃), 1.12(d, 3, CHCH₃, J=5.4 Hz), 1.09(d, 3, CHCH₃, J=5.4 Hz).

Example 14

1-(3,5-Dichlorophenyl)-2-methyl-2-propyl 2-amino-3-methylbutanoate

M.p. (oxalate) 136°–138° C.

Example 15

1-(4-Chlorophenyl)-2-methyl-2-propyl SS/RS-2-amino-3-methylpentanoate

M.p. (oxalate) 106.5°–108.5° C. ¹H NMR (200 MHz, CDCl₃) δppm 7.40, 7.32 (AA'BB', 4, C₆H₄), 3.31(d, 1,

CCH,

J=3.7 Hz), 3.19(d, 1,

CCH,

J=4.9 Hz), 3.08, 2.94(AB, 2, benzylic J=13.4 Hz), 3.08, 2.92(AB, 2, benzylic, J=13.4 Hz), 1.7(m, 1,

CH—CHC), 1.5(s, 2, NH₂), 1.49(s, 3, CCH₃), 1.43 (s, 3, CCH₃), 1.25(m, 2, CH₂), 0.9(d+t+t, 6, CH₃CH+CH₃CH₂), 0.79(d, 3, CHCH₃, J=6.8 Hz).

Example 16

1-(3,4-Dichlorophenyl)-2-methyl-2-propyl 2-aminobutanoate

M.p. (HCl salt) 107.5°–110.0° C. ¹H NMR (200 MHz, CD₃OD) HCl salt δppm 7.56(d, 1, 5-phenyl, J=8.3 Hz), 7.51(d, 1, 2-phenyl J=2.0 Hz), 7.30(dd, 1, 6-phenyl, J=8.3 Hz, 2.0 Hz), 3.98(t, 1,

CCH,

J=8.0 Hz), 3.19(AB, 2, benzylic, J=14 Hz), 1.98(quintet, 2, CH₂, J=7.3 Hz), 1.65(s, 3, CCH₃), 1.60(s, 3, CCH₃), 1.04(t, 3, CH₃, J=8.2 Hz).

Example 17

1-(4-Fluorophenyl)-2-methyl-2-propyl 2-amino-4-methylpentanoate

M.p. (oxalate) 137°–141° C. ¹H NMR (200 MHz, CD₃OD) oxalate δppm 7.34, 7.12(m, 4, C₆H₄), 3.89(t, 1, COCH, J=7.1 Hz), 3.18(s, 2, benzylic), 1.7(m, 3, CH₂CH), 1.62(s, 3, CCH₃), 1.59(s, 3, CCH₃), 1.01(d, 6, CH(CH₃)₂, J=5.9 Hz).

Example 18

1-(3-Trifluoromethyl)-2-methyl-2-propyl 2-aminobutanoate

M.p. (HCl salt) 149.5°–150.0° C. ¹H NMR (200 MHz, CDCl₃) δppm 7.44, 7.39(m, 4, arom.) 3.25(dd, 1,

CCH,

J=5.6 Hz, 7.1 Hz), 3.15, 3.05(AB, 2, benzylic, J=13.6 Hz) 1.65(m, 2, CH₂), 1.52(s, 2, NH₂), 1.51(s, 3, CCH₃), 1.47(s, 3, CCH₃), 0.90(t, 3, CH₃, J=7.6 Hz).

Example 19

1-(3-Trifluoromethyl)-2-methyl-2-propyl 2-aminopentanoate

M.p. (oxalate) 116.5°–117.5° C. ¹H NMR (200 MHz, CD₃OD) oxalate δppm 7.63(m, 4, arom), 3.98(t, 1,

CCH,

J=5.6 Hz), 3.28(s, 2, benzylic), 1.81(m, 2, CHCH₂), 1.67(s, 3, CCH₃), 1.61(s, 3, CCH₃), 1.39(m, 2, CH₂CH₃), 0.97(t, 3, CH₃, J=7.3 Hz).

Example 20

1-(4-Flurophenyl)-2-methyl-2-propyl (S)-2-amino-4-methylpentanoate

N-tert-Butoxycarbonyl-L-leucine (N-Boc-L-leucine) (0.3 g, 1.3 mmol) 1-(4-fluoro-2-methyl-2-propanol (0.39 g, 2.6 mmol) and dimethyl aminopyridine (0.015 g, 0.13 mmol), were dissolved in 3 ml of benzene. The solution was cooled in an ice bath and dicyclohexylcarbodiimide (DCC) (0.28 g, 1.35 mmol) was added under stirring. The solution was stirred during 48 h at room temperature. Dicyclohexylurea was removed by filtration and washed with benzene (2×5 ml). The filtrate was washed sucessively with HCl (0.5M, 10 ml×3), NaHCO₃ (5%, 10 ml×3) and water (10 ml×2). The organic phase was dried and the solvent was evaporated. The resulting ester (0.24 g) was purified by flash chromatography with hexane: ethylacetate 9:1 as eluent to yield 0.14 g (29%) of 1-(4-fluorophenyl)-2-methyl-2-propyl 2-[(N-Boc)amino]-4-methylpentanoate. ¹H NMR (200 MHz CDCl₃) δppm 7.15(dd, 2, 3,5-phenyl, J=8.9 Hz, 5.4 Hz), 6.97(t, 2, 2,6-phenyl, J=8.8 Hz), 4.85(d, 1, NH, J=8 Hz), 4.18(m, 1, CCH), 3.09, 2.93(AB, 2, benzylic, J=15 Hz), 1.62(m, 3, CH₂CH), 1.46(s, 3, CCH₃) 1.45(s, 9, (CH₃)₃), 1.42(s, 3, CCH₃), 0.93(d, 2, CHCH₃, J=5.4 Hz), 0.89(d, 2, CHCH₃, J=5.6 Hz).

The product obtained above was dissolved in trifluoroacetic acid (1 ml) and the mixture was stirred for 1 h at room temperature. The trifluoro acetic acid was evaporated and the residue was dissolved in diluted NH₃/diethyl ether. The organic phase was separated, washed with water and dried and the diethyl ether was evaporated. The optical purity, which was determined on capillary GC after coupling with Moshers acid, was >95%. The amine was precipitated as an oxalate and recrystallized from isopropanol.

M.p. (oxalate) 137°–141° C. ¹H NMR (200 MHz, CD₃OD) oxalate δppm 7.34, 7.12(m, 4, C₆H₄), 3.89(t, 1, COCH, J=7.1 Hz), 3.18(s, 2, benzylic), 1.7(m, 3, $CH_2CH$), 1.62(s, 3, $CCH_3$), 1.59(s, 3, $CCH_3$), 1.01(d, 6, $CH(CH_3)_2$, J=5.9 Hz).

Example 21

1-(4-Chlorophenyl)-2-methyl-2-propyl (S)-2-aminopentanoate 1-(4-Chlorophenyl)-2-methyl-2-propyl (S)-2-aminopentanoate was obtained analogous to Example 20 with an optical purity of 78% e.e. The obtained product was precipitated as a tartrate with L-(+)-tartaric acid and recrystallization from ethanol:water 2:1. E.e. (after recrystallization >98%. M.p. (tartrate) 124°-126° C. $^1H$ NMR was the same as according to example 10.

Example 22 (Method A)

1-(3,4-Dichlorophenyl)-2-methyl-2-propyl 2-aminobutanoate 1-(3,4-dichlorophenyl)-2-methyl-2-propyl 2-[(N-benzyloxycarbonyl)]amino butanoate $^1H$ NMR (200 MHz, $CDCl_3$) δppm 7.35, 7.01(m, 8, $C_6H_5$) and $C_6H_3$), 5.26(d, 1, NH, J=10 Hz), 5.12(s, 2, $OCH_2$), 4.21(m, 1, COCH), 3.02, 2.88(AB, 2, benzylic, J=13.7 Hz), 1.77, 1.77, 1.65(m, 2, $CH_2$), 1.49(s, 3, $CCH_3$), 1.42(s, 3, $CCH_3$), 0.88(t, 3, $CH_3$, J=/0.3 Hz)) was dissolved in 0.2 M HCl/ethanol and hydrogenated in the presence of Pd/C to give the title compound. M.p. (HCl salt) 113.5°-116.0° C. $^1H$ NMR according to Example 16 above.

Example 23 (Method A)

1-(4-Fluorophenyl)-2-methyl-2-propyl 2-aminobutanoate 1-(4-Fluorophenyl)-2-methyl-2-propyl 2-bromobutanoate was prepared in analogy with the method described for compound 1 by Lindberg et al in the Journal of Medicinal Chemistry 21, p. 448-456 (1978). $^1H$ NMR (60 MHz, $CDCl_3$) δ ppm 7.2-7.0(m, 4,Ar), 4.1(t, 1, CHBr), 3.1 (s, 2, benzylic), 1.9(m, 2, $CH_2$), 1.0(t, 3, $CH_3$)).

The compound obtained above (951 mg, 3.0 mmol) was added to a solution of sodium nitrite (359 mg, 5.2 mmol) and phloroglucinol (403 mg, 3.2 mmol) in dimethylformamide (10 ml) at ambient temperature. After stirring for 3 h the mixture was poured into cold water and extracted with ether. After drying ($Na_2SO_4$) and evaporation of ether an oil of 1-(4-fluroophenyl)-2-methyl-2-propyl 2-nitrobutanoate was obtained. Yield: 750 mg (88). The $^1H$ NMR (60 MHz, $CDCl_3$) δ ppm 7.2-7.0(m, 4, Ar), 5.0(t, 1, $CHNO_2$), 3.0 (s, 2, benzylic), 1.9(m,2, $CH_2$), 1.0(t, 3, $CH_3$).

The compound isolated above (700 mg, 2.5 mmol) dissolved in acetic acid (15 ml) was hydrogenated over 10% Pd/C (300 mg) at 50° C. and 50 psi pressure for 24 h. After filtration and evaporation of the solvent the residue was taken up in ether and extracted with 2N hydrochloride acid. The acid phase was made alkaline and extracted with ether, whereafter the organic phase was dried and evaporated to give the title compound as an oil. Yield: 75 mg (12%). $^1H$ NMR was identical to the spectrum of the product obtained in Example 2.

Example 24

1-(4-Fluorophenyl)-2-methyl-2-propyl 2-aminobutanoate

The compound obtained in the first step of Example 22 namely 1-(4-fluorophenyl)-2-methyl-2-propyl 2-bromobutanoate (1.58 g, 5.0 mmol), and benzylamine (2.14 g, 20 mmol) were dissolved in ethanol (40 ml) and the solution was refluxed for 24 h. The solvent was evaporated, the residue was taken up in water, the pH was adjusted to 4.0 and the aqueous phase was extracted with ether. The organic solvent was dried and evaporated to give a yellow oil of 1-(4-fluorophenyl)-2-methyl-2-propyl 2-benzylaminobutanoate. Yield: 1.47 g (85%). $^1H$ NMR (60 MHz, $CDCl_3$) δ ppm 7.4-7.0(m, 9, Ar), 4.1(m, 1, CH), 3.7 (d, 2, $ArCH_2NH$), 3.1(s, 2, $ArCH_2C$), 1.9(m, 2, $CH_2$), 1.5-1.5(m, 7, $C(CH_3)_2$+NH), 0.9(t, 3, $CH_3$)).

The compound obtained above (343 mg, 1.0 mmol) was dissolved in ethanol (10 ml) and was with 10% Pd/C (100 mg) as a catalyst hydrogenated at ambient temperature and pressure for 28 h. After filtration and evaporation of the solvent, the residue was taken up in ether and extracted with 2N hydrochloric acid. The acid phase was made alkaline and extracted with ether. The ether solution was dried and the solvent evaporated to give the title compound as an oil. Yield: 178 mg (70%). The $^1H$ NMR spectrum was identical with the spectrum of the product obtained in Example 2.

Example 25 (Method B)

1-(3,5-Dichlorophenyl-2-methyl-2-propyl 2-amino-3-methylbutanoate

To 1-(3,5-dichlorophenyl)-2-methyl-2-propyl 2-oxo-3-methylbutanoate (80 mg, 0.25 mmol) and ammonium acetate (154 mg, 2.0 mmol) dissolved in methanol (10 ml), sodium cyanoborohydride (19 mg, 0.3 mmol) was added. After stirring at room temperature for 20 h the solvent was evaporated and the residue dissolved in $H_2O$ and ether and made alkaline. After a second extraction with ether, the combined ether extracts were dried and evaporated. The residue which was the title product was isolated as an oil which was identical with the compound obtained in example 14. Yield: 56 mg (70%).

Examples 26 and 27 (Method E)

The racemate of 1-(4-chlorophenyl)-2-methyl-2-propyl 2-amino-3-methyl-butanoate was prepared according to the method described in the above cited Journal of Medicinal Chemistry and separated into its enantiomers by fractionated crystallizations of the L-(+)- and D-(−)-tartrates from ethanol: water in the proportions 1:1.

The (+) enantiomer (Example 26) had the following data: M.p. (L-(+)-tartrate) 142.5°-144° C., $[α]^{25}$=+25.4°

$^1H$ NMR (200 MHz, $CDCl_3$) δ ppm 7.15, 7.02 (AA'BB', 4, $C_6H_4$), 3.02 (d, 1, COCH), 2.98, 2.85 (AB, 2, benzylic), 1.85 (m, 1, CH) 1.45 (s(broad), 2, $NH_2$), 1.38 (s, 3, $CCH_3$), 1.33 (s, 3, $CCH_3$), 0.85 (d, 3, $CHCH_3$).

The (−)enantiomer (Example 27) had the following data: M.p. (D-(−)-tartrate) 146.0°-147.5° C., $[α]^{25}$=−25.7. $^1H$ NMR was the same as in Example 26.

Example 28

(+)-1-(4-Chlorophenyl)-2-methyl-2-propyl 2-amino-3-methylbutanoate (Method A)

1-(4-chlorophenyl)-2-methyl-2-propyl 2[(N-trifluoroacetyl)amino]-3-methyl-butanoate ($^1H$ NMR (200 MHz, $CDCl_3$) δ ppm: 6.75 (s(broad), 1, NH)) was treated with a solution of 7% $K_2CO_3$ in methanol/water 6/4 for 6 h at room temperature. After evaporation the residue was extracted with ether, which was dried and evaporated to give the title compound as an oil. $^1$H NMR was the same as according to Example 26. The optical purity, which was determined on capillary GC coupling with Moshers acid was 60%.

Pharmaceutical preparations

The following examples illustrate the preparation of pharmaceutical compositions to be used in the method of the invention. For the preparation of tablets the following compositions can be made.

Example 29

| | |
|---|---|
| 1-(4-Fluorophenyl)-2-methyl-2-propyl (S)-2-amino-4-methylpentanoate. | 50 g |
| Lactose | 85 g |
| Potato starch | 40 g |
| Polyvinylpyrrolidone | 5 g |
| Microcrystalline cellulose | 18 g |
| Magnesium stearate | 2 g |

Example 30

| | |
|---|---|
| 1-(4-Chlorophenyl)-2-methyl-2--propyl (S)-2-amino-3-pentanoate | 100 g |
| Lactose | 90 g |
| Potato starch | 50 g |
| Polyvinylpyrrolidone | 5 g |
| Microcrystalline cellulose | 23 g |
| Magnesium stearate | 2 g |

From the above compositions 1000 tablets can be made, containing 50 mg and 100 mg of active substance, respectively. If desired, the obtained tablets can be film coated with e.g. methyl cellulose in an organic solvent or using water.

Example 31

Example of solution for intravenous or intramuscular injection

Compound according to Example 1: 60 g
Water for injection: ad 1000 ml.

The active compound shall be dissolved in water to a final volume of 1000 ml and the solution filtered through a sterile 0.22 μm filter and aseptically dispensed into 1 ml sterile ampoules, which then are sealed.

PHARMACOLOGICAL METHODS

Inhibition of the Synaptosomal Uptake of Monoamines

Crude synaptosome preparations from rat cerebral cortex were made by homogenizing the tissues in 10 volumes of ice-cold 0.32M sucrose with all-glass Potter'-Elvehjem's homogenizers. The homogenates were centrifuged at 800 g at +2° C. for 10 min. The supernatants were centrifuged at 12000 g at +2° C. for 10 min, and the pellets were rehomogenized in 0.32M sucrose to the original volume. The incubation of the preparations with [$^{14}$C]serotonin plus [$^3$H]noradrenaline with final concentrations of 50 nM of each amine was performed in a Micronic PPN Storage-Block-96 (Flow Laboratories) with 8×12 wells using two rows at each incubation. Four to five different concentrations of two test compounds in duplicates were examined at each incubation. Fifty microliters of the synaptosomal preparation, 400 μl of the Krebs-Henseleit's buffer, pH 7.4, containing 5.6 mM glucose, 1.1 mM ascorbic acid, 0.13 mM disodium edetate, and 50 μM pargyline, and 25 μl of the inhibitor or distilled water were added to the wells. The solutions were mixed by vortexing the block for 10 s. After 10-min preincubation at 37° C. in a water bath, 25 μl of the solutions of the radioactively labeled amines was added to the two rows with a Titretec Multicannel Pipette, type 12-Channel (Flow Laboratories). The reaction was immediately started by vortexing the block for 10 s on a Super-Mixer, and the incubation was continued for 2 min at 37° C. The uptake reaction was stopped by filtration and washing for 15 s with ice-cold 0.15M NaCl through a Whatman GF/B glass filter paper in a 24-channel Cell Harvester (Brandel) using the standard harvesting probe. The filters were left to dry in room temperature for about 1 h. The punched filters were transformed to counting vials, 10 mL of the scintillation liquid (Aquasol, NEN) was added, and vials were shaken and allowed to stand for 1 h before counting. The radioactivety was measured in a Packard Tri Carb liquid scintillation photometer. The active uptake of the amines was defined as the difference between the accumulation of the radioactivity in the absence (quadriplicates) and the presence (quadriplicates) of selective uptake inhibitors, determined at each incubation. These inhibitors were citalopram (0.3 μM) for the serotonin uptake and maprotiline (1 μM) for the norepinephrine uptake. The inhibition was calculated in percent of the active uptake. The IC$_{50}$ values were obtained from log concentration-response curves.

Potentiation of cholinergic responses

Studies on oxotremorine-induced tremor in rats

Male rats (Sprague Dawley Alab Laboratorietjänst AB, Sollentuna, Sweden) weighing 150–180 g, 35–40 days of age, were used. The animals were allowed free access to food (R3, Ewos AB, Södertälje, Sweden) and water until the start of the experiments. The test compounds were injected intraperitoneally (i.p.) 30 min before injection of oxotremorine into the neck (s.c.). Tremor intensity was assessed visually for a 60 min period following the injection of oxotremorine in rat housed in Macrolon cages (25×25×30 cm) (tree per cage). The treshold dose of oxotremorine for eliciting tremor in rat is 200 μg/kg.

Tremor intensity was scored using the following rating scale: 0=no tremor; 1=slight tremor (moderate, discontinuous tremor); 2=strong tremor (intense, continuous tremor involving the whole body). The animals were scored 5, 10, 15, 30 and 60 min after injection of oxotremorine. The tremor was scored for a period of 30 seconds.

The values for each observation were summed over the entire observation period (5–60 min) and their median values for each group were calculated (total median score). Mann-Whitney U-test (two-tailed) was used to determine differences between the control oxotremorine group and test groups receiving the compounds+oxotremorine. It should be noted that a control group receiving oxotremorine alone was always run concurrently with each compound tested.

The lowest dose causing a significant ($p<0.05$) potentiation of the oxotremorine response was determined from log-dose response curves.

In the following Table 2 data are illustrated on the testing for the inhibition of synaptosomal uptake of monoamines and potentiation of oxotremorine induced tremor in rat of compounds of the general formula XII.

TABLE 2

$$\text{X} \underset{\text{Y}}{\overset{}{\bigcirc}} -CH_2-\underset{\underset{CH_3}{|}}{\overset{\overset{CH_3}{|}}{C}}-O-\overset{\overset{O}{\|}}{C}-\underset{\underset{R}{|}}{CH}-NH_2 \quad XII$$

| Compound according to Example No or ref | X | Y | R | Inhibition of synaptosomal uptake, EC$_{50}$, ($\mu$M) noradrenalin | serotonin | Potentiation of OTMN in rat mg/kg tremor |
|---|---|---|---|---|---|---|
| Alaproclate | 4-Cl | H | CH$_3$ | >10 | 0.12 | 5.0 |
| 1 | 4-Cl | H | C$_2$H$_5$ | 8.0 | 2.8 | 2.5 |
| 2 | 4-F | H | C$_2$H$_5$ | 7.0 | 3.0 | 10 |
| 3 | 4-F | H | C$_3$H$_7$ | 3.2 | 6.0 | 10 |
| 4,8 | 4-Cl | H | C$_3$H$_7$ | 1.5 | 2.3 | 2.5 |
| 5 | 4-Cl | H | CH$_2$—CH=CH$_2$ | 2.5 | 3.6 | 20 |
| 7 | 4-Cl | H | CH$_2$C≡CH | >10 | >10 | 10 |
| 11 | 4-Cl | H | CH$_2$CH(CH$_3$)$_2$ | 3.4 | 8.0 | 10 |
| 12 | 4-Cl | H | CH(CH$_3$)(C$_2$H$_5$) | 3.2 | 6.5 | 20 |
| 13 | 4-F | H | CH(CH$_3$)$_2$ | 2.9 | 10 | 20 |
| 14 | 3-Cl | 5-Cl | CH(CH$_3$)$_2$ | >10 | 4.0 | 10 |
| 15 | 4-F | H | CH(CH$_3$)(C$_2$H$_5$) | 3.1 | 8.0 | 10 |
| 26 | (+)4-Cl | H | CH(CH$_3$)$_2$ | 1.8 | 8.7 | 20 |
| 27 | (−)4-Cl | H | CH(CH$_3$)$_2$ | 1.7 | 3.3 | 10 |

Discussion

As can be seen from table 2 the compounds according to the invention are at least tenfold less active than alaproclate in the ability to inhibit 5 HT uptake into synaptosomes.

Both alaproclate and the compounds according to the invention enhance the tremor response induced by a treshold dose of the muscarinic agonist oxotremorine (OTMN). Thus, the compounds according to the invention are selective in potentiating cholinergic responses in contrast to alaproclate.

Accordingly, the inherent ability for the compounds according to the invention to affect the cholinergic system without direct interference with the serotonergic system makes it possible to treat patients with senile dementia and other disorders related to central cholinergic pathways in a more adequate way involving less side-effects due to serotonergic mechanisms.

We claim:

1. A method for exerting an effect on the central nervous system of mammals by potentiating cholinergic responses comprising administering to a patient having mental disturbances an amount effective to potentiate the cholinergic response of a compound or a pharmaceutically acceptable salt having the formula:

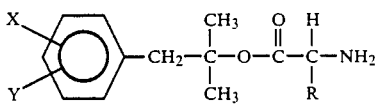

wherein X and Y are halogen, CF$_3$ or hydrogen provided that both X and Y are not hydrogen.

* * * * *

UNITED STATES PATENT AND TRADEMARK OFFICE
CERTIFICATE OF CORRECTION

PATENT NO. : 4,990,534

DATED : February 5, 1991

INVENTOR(S) : Gerd M. Hallnemo; Thomas Högberg; Ulf H. Lindberg; Carl B.J. Ulff; Sven Ove Ögren It is certified that error appears in the above-identified patent and that said Letters Patent is hereby corrected as shown below:

col. 2, lines 27-34,

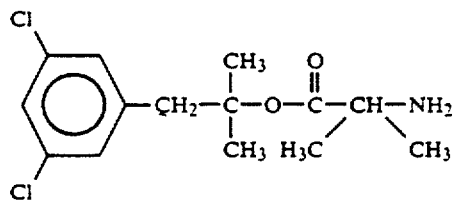

should read --

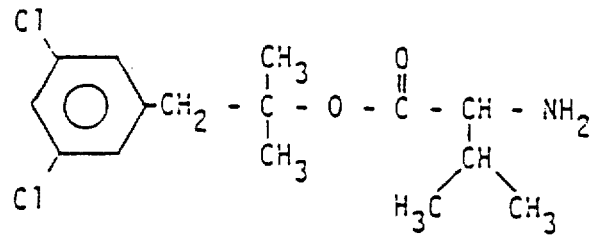

--;

UNITED STATES PATENT AND TRADEMARK OFFICE
CERTIFICATE OF CORRECTION

PATENT NO. : 4,990,534

DATED : February 5, 1991

INVENTOR(S) : Gerd M. Hallnemo; Thomas Högberg; Ulf H. Lindberg; Carl B.J. Ulff; Sven Ove Ögren It is certified that error appears in the above-identified patent and that said Letters Patent is hereby corrected as shown below:

Col. 10, line 29, "(1S,2S,5S)-(-(-2-hydrox" should read --(1S,2S,5S)-(-)-2-hydrox--;

Col. 15, line 50, "750 mg (88)" should read --750 mg (88%)--;

Signed and Sealed this

Fifteenth Day of September, 1992

Attest:

DOUGLAS B. COMER

Attesting Officer

Acting Commissioner of Patents and Trademarks